United States Patent [19]

Besancon et al.

[11] Patent Number: 4,725,618

[45] Date of Patent: Feb. 16, 1988

[54] USE OF N-(1-ALLYL-2-PYRROLIDINYLMETHYL) 2-METHOXY 4-AMINO 5-METHYLSULPHAMOYL BENZAMIDE IN THE TREATMENT OF PARKINSON'S DISEASE

[75] Inventors: Denis Besancon, Paris, France; Brenda Costall; Robert J. Naylor, both of West Yorkshire, United Kingdom; Peter Jenner; Charles D. Marsden, both of London, United Kingdom

[73] Assignee: Societe D'Etudes Scientifiques Et Industrielles De L'Ile-De-France, Paris, France

[21] Appl. No.: 885,965

[22] Filed: Jul. 15, 1986

[30] Foreign Application Priority Data

Jul. 15, 1985 [FR] France ............................ 85-10802

[51] Int. Cl.$^4$ .............................................. A61K 31/40
[52] U.S. Cl. ......................................................... 514/428
[58] Field of Search ................................ 514/408, 428

[56] References Cited

U.S. PATENT DOCUMENTS

| | | | |
|---|---|---|---|
| 3,342,826 | 9/1967 | Miller et al. | 260/294 |
| 4,263,316 | 4/1981 | Thominet et al. | 514/428 |
| 4,405,636 | 9/1983 | Perrot et al. | 514/428 |
| 4,499,019 | 2/1985 | Thominet et al. | 514/428 |
| 4,550,179 | 10/1985 | Perrot et al. | 548/571 |

*Primary Examiner*—Stanley J. Friedman
*Attorney, Agent, or Firm*—Fitzpatrick, Cella, Harper & Scinto

[57] ABSTRACT

The use of N-(1-allyl-2-pyrrolidinylmethyl) 2-methoxy 4-amino 5-methylsulphamoyl benzamide to treat Parkinson's disease.

1 Claim, No Drawings

USE OF N-(1-ALLYL-2-PYRROLIDINYLMETHYL) 2-METHOXY 4-AMINO 5-METHYLSULPHAMOYL BENZAMIDE IN THE TREATMENT OF PARKINSON'S DISEASE

The present invention concerns a novel application of N-(1-allyl-2-pyrrolidinylmethyl)2-methoxy 4-amino 5-methysulphamoyl benzamide. This compound is known to the art as set forth in U.S. Pat. Nos. 4,405,636 and 4,550,179. In addition, that compound is useful as a platelet anti-aggregating agent, as recited in copending allowed application Ser. No. 638,403, filed Aug. 7, 1984, now U.S. Pat. No. 4,607,047.

The results of biochemical and clinical studies have demonstrated the effectiveness thereof in dealing with Parkinson's disease. Parkinson's disease is characterized by tremors, akinesia and rigidity. Biologically, the disease is characterized by reduced dopamine levels in negrostriatal tissue.

This compound exhibits a particularly marked indirect dopaminergic agonistic effect, but it does not block the post-synaptic dopaminergic receptor. That effect was unexpected from the results which are usually obtained with conventional benzamides which are known to block that receptor.

The usual methods of treating Parkinson's disease aim at stimulating the post-synaptic dopaminergic receptor, and the administration of a potentially blocking product was, a priori, not indicated.

The known treatments for Parkinson's disease comprise use of anticholinergic substances; L-dopa and associations thereof with decarboxylase inhibitors; and true dopaminergic agonistic agents such as bromocryptine, lergotrile, piribedil and amantadine.

By virtue of their capacity to block the post-synaptic receptor, conventional benzamides were generally considered as being responsible for the Parkinson syndrome.

In contrast thereto, studies of the compound of the invention have revealed its indirect dopaminomimetic properties and its incapacity to block the post-synaptic receptor. Accordingly, the compound of the invention acts to induce an increase in the striatal dopamine level.

The activity of the compound, in accordance with the invention, was demonstrated by means of an experimental animal model which is known to have a predictable clinical correspondence. The study involved intoxication, by MPTP (or 1-methyl-4-phenyl-1,2, 3, 6-tetrahydropyridine), which, in small doses, selectively destroys the pigmented dopaminergic neurons, both in monkeys and in man.

MPTP thus reproduces the physical and biochemical signs of Parkinson's disease, including the disease's capacity for therapeutic response to L-dopa ("MPTP Parkinsonism", see British Medical Journal, Vol. 289, pages 1401–1402, November 1984). A unique procedure permitting experiments to be carried out on rats, which are not the usual model with respect to responses with MPTP, was developed. The procedure comprises perfusing the selective neurotoxin, MPTP, for a period of 13 days at the level of the substantial nigra of a male rat. Toxic effects (hypokinesia and bradykinesia) appear about 12 hours after the commencement of the perfusion operation, and they persist for the period of 13 days and even longer (up to 40 days after the end of the perfusion operation).

In particular, to execute the MPTP procedure, cannulae are implanted into the substantia nigra of test animals, as rats. MPTP is infused into the test animals employing a minipump operated at the rate of 0.48 microlites per hour for 13 days. The test compound is injected subcutaneously at a dose of 1 mg/kg/day. Akinesia, i.e. hypokinesia and/or bradykinesia, of the test animal is then measured as a reduction in movements of the animal in individual photocell cages. All test measurements are made in the period from day 2 to day 10 of post-infusion of MPTP. The test compound is injected on day 5 to day 7 of post-infusion.

It is possible to achieve quasi-suppression of hypokinesia and bradykinesia by a levodopa/benserazide treatment. Replacing the L-dopa by the substance to be studied, therefore, makes it possible to evaluate the anti-Parkinsonism activity of that substance. The same results are obtained with a Marmoset monkey, which is the usual model for that type of experiment.

The compound of this invention, in doses of 1 mg/kg/SC, produces an antagonism in respect of the akinesia induced by the MPTP, in the same manner as a treatment using L-dopa (100 mg/kg/IP) and pergolide (0.5 mg/kg/IP), in rats and monkeys.

Studies with respect to "binding", which were carried out in-vitro, demonstrated that the compound of the invention acts as a specific dopamine D2 antagonistic agent with moderate effects on the alpha receptors.

The effect of the compound of the invention differs from conventional neuroleptic agents by its action on the central dopaminergic receptors. Its central anticholinergic action is zero, as is demonstrated by the tests with oxotremorine in a mouse.

The following experimental results with N-(1-allyl-2-pyrrolidinylmethyl)2-methoxy-4-amino-5-methylsulphamonyl benzamide were observed:

(1) Only very high doses ($\geq 80$ mg/kg/IP) reduced spontaneous motility in mice employing the test procedure in J. Pharm. Exp. Ther. 101, pp. 156–162 (1951).

(2) No anomaly in coordination or forced motility was observed, in relation to mice subjected to the conventional rotating rod test, after the administration of doses attaining levels of 80 mg/kg/IP employing the test procedure in J. Pharm. Exp. Ther. 121, pp. 354–361 (1957).

(3) No catalepsy was induced in a rat, even at doses of 200 mg/kg/SC using the test in Arzneimittel Forsch. 12, pp. 964–968 (1962).

(4) Antagonism to climbing behavior (mice) and stereotypies (rats and mice), which are induced by apomorphine, occurred only at very high doses of the compound. Even then, this effect was only partial with regard to inhibition of stereotypies, see Eur. J. Pharm. 50, pp. 291–300 (1978).

(5) Antagonism to vomiting induced in a dog by apomorphine according to J. Pharm. Exp. Ther. 98, pp. 245–250 (1950) and rye ergot in accord with Arzn.Forsch. 12, pp. 964–968 (1962), or hypothermia induced in a mouse by apomorphine, utilizing the test of Eur. J. Pharm 50, pp. 291–200 (1978) at inhibiting doses 50 (ID.$_{50}$) of 1 ug/kg/SC, 48 ug/kg/SC and 1.9 mg/kg/IP, demonstrate the powerful antidopaminergic effect on the area postrema and the hypothalamus. In the hypophysis, a powerful antidopaminergic effect was also revealed by the rise in the serum prolactive level which is found in a male rat, after IV injection of a very small dose of the product of the invention (3 ug/kg). Such data illustrates the powerful peripheral antidopaminergic action of the compound.

(6) In small doses, the compound potentialises the stereotypies induced in a rat by small doses of apomorphine in accordance with Arzn. Forsch. 27(2), pp. 1968–1979 (1977) and the chewing or nibbling movements induced in a mouse by apomorphine employing the test procedure in Brit. J. Pharm. 34(1), pp. 219–220 (1968). Conventional neuroleptics (haloperidol and chloropromazine) or even sulpiride, a benzamide, are inactive under those conditions.

(7) In small doses, the compound of the invention potentialises, in a rat, buccal stereotypies induced by small doses of d-amphetamine as carried out in Brit. J. Pharm. 23(2), pp. 330–350 (1964). At the same doses, conventional neuroleptics and sulpiride do not potentialise such behavior.

(8) In contrast to sulpiride, for example or other benzamides, intrastriatal injection does not induce an asymmetry behavior in a rat either in spontaneous circular movements, or, after administration of amorphine, even in doses of higher than 5 ug.

The results indicate that the compound does not block the striatal post-synaptic receptors.

The indirect dopaminomimetic activating effect and the absence of striatal post-synaptic blocking of the compound serve as a basis for using it to treat Parkinson's disease.

On the basis of the animal experiment results, potentiation of conventional anti-Parkinsonian agents, added to the possible suppression of peripheral side effects inherent in such agonistic agents (vomiting and hypotension) was envisaged by virtue of the powerful peripheral blocking effect (dopamine) observed with the benzamide compounds.

That hypothesis was confirmed in pharmacological investigations. The compound of the invention was administered and increased spontaneous activity as well as the activity induced by apomorphine. This established the dopamine agonistic effect (increase in locomotion activity, with doses varying from 0,001 mg/kg to 40 mg/kg/SC).

Clinical tests make it possible to emphasize the absence of extrapyramidal manifestations. The therapeutic doses which can be recommended vary from 10 to 100 mg/day in one or more doses, depending on the seriousness of the disease.

The compound of the invention can be administered in any number of conventional forms such as capsules, tablets, pills, in granulated form or as an injectable solution. Many methods for compounding these preparations are well-known to the art. Substances which are inert relative to the compounds of the invention can be used in these preparations, such as lactose, magnesium stearate, starch, talc, cellulose, levilite, alkali metal lauryl-sulphates, saccharose and other vehicles commonly employed in pharmaceutical preparations.

The examples which follow illustrate several possible pharmaceutical preparations.

EXAMPLE I

Tablets

| | |
|---|---|
| N—[1-allyl-2-pyrrolidinylmethyl] 2-methoxy 4-amino 5-sulphamoylbenzamide | 100 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

EXAMPLE II

Capsules

| | |
|---|---|
| N—[1-allyl-2-pyrrolidinylmethyl] 2-methoxy 4-amino 5-sulphamoylbenzamide | 50 mg |
| microcrystalline cellulose | 50 mg |
| methylcellulose 1500 cps | 1 mg |
| magnesium stearate | 5 mg |
| talc | 2 mg |
| for 1 capsule. | |

EXAMPLE III

Injectable Solution

| | |
|---|---|
| N—[1-allyl-2-pyrrolidinylmethyl] 2-methoxy 4-amino 5-sulphamoylbenzamide | 40 mg |
| 1N hydrochloric acid | 0.1 ml |
| sodium chloride | 14 mg |
| for 2 ml. | |

EXAMPLE IV

Injectable Solution

| | |
|---|---|
| N—[1-allyl-2-pyrrolidinylmethyl] 2-methoxy 4-amino | 100 mg |
| 1N hydrochloric acid | 0.250 ml |
| sodium chloride | 8 mg |
| for 2 ml. | |

To prepare the tablets, the compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservatives are added. It is also possible to prepare the same solution without adding any preservatives: the ampoule is then filled under nitrogen and sterilized or ½ hour at 100° C.

The pharmacologically acceptable salts of the compound of the invention include the non-toxic acid addition salts formed by reacting the benzamide of the invention with the desired acid. The acid may be an inorganic acid, such as sulfuric, sulfamic, nitric, hydrobromic, hydrochloric, phosphoric and the like or an organic acid, such as citric, tartaric, lactic, acetic, succinic, fumaric, maleic, benzoic and the like.

The pharmacologically acceptable salts of the compound of the invention also include the non-toxic quaternary ammonium salts produced by reacting the benzamide with an aliphatic or aromatic alkylating agent, such as methyl chloride, methyl bromide, dimethyl sulfate, methyl p-toluene sulfonate and the like. In addition, the benzamide compound includes the N-oxides formed by utilizing the conventional oxidizing agents; see, for example, U.S. Pat. No. 3,839,330, issued Oct. 1, 1974.

What is claimed is:

1. A method for treating the symptoms of Parkinson's disease by administering to a patient having said symptoms a therapeutically effective amount sufficient to suppress said symptoms of N-(1-allyl-2-pyrrolidinyl methyl)-2-methoxy-4-amino-5-methylsulphamoyl benzamide or a pharmacologically acceptable salt thereof.

* * * * *